United States Patent
Reed et al.

(10) Patent No.: US 9,990,333 B1
(45) Date of Patent: Jun. 5, 2018

(54) SYSTEMS AND METHODS FOR SYNCHRONIZING THE KINEMATICS OF UNCOUPLED, DISSIMILAR ROTATIONAL SYSTEMS

(71) Applicants: Kyle B. Reed, Tampa, FL (US); Ismet Handzic, Lutz, FL (US)

(72) Inventors: Kyle B. Reed, Tampa, FL (US); Ismet Handzic, Lutz, FL (US)

(73) Assignee: University of South Florida, Tampa, FL (US)

( * ) Notice: Subject to any disclaimer, the term of this patent is extended or adjusted under 35 U.S.C. 154(b) by 374 days.

(21) Appl. No.: 14/724,458

(22) Filed: May 28, 2015

Related U.S. Application Data

(60) Provisional application No. 62/003,738, filed on May 28, 2014.

(51) Int. Cl.
  *G06G 7/48* (2006.01)
  *G06F 17/10* (2006.01)
  *D06F 37/22* (2006.01)
  *A61F 2/60* (2006.01)

(52) U.S. Cl.
  CPC .............. *G06F 17/10* (2013.01); *A61F 2/60* (2013.01); *D06F 37/225* (2013.01)

(58) Field of Classification Search
  CPC . A61N 5/10; G01N 11/12; B60K 6/48; B64D 31/04; H02P 6/183; B64C 27/32; F03B 15/005; A61F 2/60; D06F 37/203; D06F 37/225; G04C 3/146; G05F 1/66; F01N 11/007
  See application file for complete search history.

(56) References Cited

U.S. PATENT DOCUMENTS

| | | | |
|---|---|---|---|
| 3,698,239 A | 10/1972 | Everett | |
| 4,415,156 A | 11/1983 | Jorgensen | |
| 6,301,964 B1 | 10/2001 | Fyfe et al. | |
| 6,532,422 B1* | 3/2003 | Elgersma | D06F 37/225 68/23.2 |
| 6,535,158 B2 | 3/2003 | Wilkerson et al. | |
| 8,108,072 B2 | 1/2012 | Zhao et al. | |
| 8,573,982 B1 | 11/2013 | Chuang | |
| 8,630,763 B2 | 1/2014 | Goulding | |
| 2003/0065468 A1* | 4/2003 | Determan | D06F 37/225 702/105 |
| 2003/0093989 A1* | 5/2003 | Ueno | F01N 11/007 60/277 |

(Continued)

OTHER PUBLICATIONS

Bunnett, et al., "Huygen's Clocks", Proceedings: Mathematical, Physical and Engineering Sciences, 2019, Mar. 2002.

(Continued)

*Primary Examiner* — Kandasamy Thangavelu
(74) *Attorney, Agent, or Firm* — Thomas | Horstemeyer, LLP

(57) ABSTRACT

In one embodiment, a system or method for kinematically synchronizing uncoupled, dissimilar rotational systems pertain to modeling a first rotational system using an equation of motion to obtain a first system model, modeling a second rotational system that is physically dissimilar to the first rotational system using the equation of motion to obtain a second system model, and matching kinematic matching coefficients of the equations of motion for the first and second system models.

22 Claims, 14 Drawing Sheets

(56) References Cited

U.S. PATENT DOCUMENTS

| | | | |
|---|---|---|---|
| 2003/0101812 A1* | 6/2003 | Stalsberg | D06F 37/203 73/460 |
| 2004/0101110 A1* | 5/2004 | Eppler | G01N 23/04 378/207 |
| 2005/0147495 A1* | 7/2005 | Bittner | B64C 27/32 416/131 |
| 2005/0267644 A1* | 12/2005 | Kuwabara | F03B 15/005 700/287 |
| 2006/0184280 A1 | 8/2006 | Oddsson et al. | |
| 2010/0045218 A1* | 2/2010 | Tomigashi | H02P 6/183 318/400.02 |
| 2010/0263980 A1* | 10/2010 | Otto | F16D 11/12 192/53.363 |
| 2011/0257764 A1* | 10/2011 | Herr | A61F 2/60 623/24 |
| 2011/0315113 A1* | 12/2011 | Egle | B64D 31/04 123/342 |
| 2013/0258819 A1* | 10/2013 | Hoover | G04C 3/146 368/184 |
| 2013/0261766 A1 | 10/2013 | Langlois et al. | |
| 2013/0307449 A1* | 11/2013 | Kobayashi | B60K 6/48 318/400.02 |
| 2015/0034091 A1* | 2/2015 | Coucke | A61N 5/10 128/845 |
| 2015/0105927 A1* | 4/2015 | Baone | G05F 1/66 700/292 |

OTHER PUBLICATIONS

Dilao, R., "Antiphase and in-phase synchronization of nonlinear oscillators: The Huygenss clocks system", Choas 19, Jun. 2009.

Geyer, et al., "Complilant leg behavior explains basic dynamics of walking and running", Proceedings of the Royal Society, 273, Aug. 2006.

Handzic, et al., Comparison of the passive dynamics of walking on ground, tied-belt and split-betl treadmills, and via the gait enhancing mobile shoe (GEMS), in Proc. IEEE Int. Conf. Rehabilitation Robotics, Jun. 2013.

Hekmatfard, et al., Effects of prosthetic mass distribution on the spatiotemporal characteristics and knee kinematics of transfemoral amputee locomotion. Gait 37, 2013.

Honeycutt, et al., "Asymmetric passive dynamic walker", In Proc. IEEE Int. Conf. Rehabilitation Robotics, Jun. 2011.

Khan, et al., "Synchronization, anti-synchronization and hybrid-synchronization of a double pendulum under the effect of external forces", Int. Journal of Computational Engineering Research, 2013.

Kuo, A.D., "The six determinants of gait and the inverted pendulum analogy: A dynamic walking perspective", Human Movement Science 26, Jul. 2007.

Mongeau, et al., "Rapid inversion: running animals and robots swing like a pendulum under ledges", Plos One 7, Jun. 2012.

Nair, et al., "Stable synchronization of mechanical system networks", Journal of control optimization, 2008.

Sun, et al., "Motion synchronization for dual-cylinder electrohydraulic lift systems", Transactions on mechatronics, Jun. 2002.

Sushko, et al., "Prothesis design based on an asymmetric passive dynamic walker", In Proc. IEEE Conf. Biorob, Jun. 2012.

Frandkov, et al., "Synchronization and phase relations in the motion of two-pendulum systems", Int. Journal of Non-Linear Mechanics, Mar. 2007.

Gluck et al., "A swing-up control of a triple pendulum on a cart with experimental validation", Automotica 49, 2013.

Gregg, et al., "The basic mechanics of bipedal walking lead to asymmetric behavior", In Proc. IEEE Int. Conf. Rehabilitation Robotics, 2011.

Gregg, et al., "On the mechanics of functional asymmetry in bipedal walking", IEEE Transactions on Biomedical Engineering 59, 2012.

Gibson-Horn, C., "Balancebased torso-weighting in a patient with ataxia and multiple sclerosis: A case report", Journal of Neurologic Physical Therapy 32, 2008.

Handzic, et al., "Design and pilot study of a gait enhancing mobile shoe", J. of Behavioral Robotics 2, 4, 2011.

Bundey, et al., "n the swing mechanics of a matched set of golf clubs", Research quarterly for Exercise and Sport 53, 1982.

Olusola, et al., "Global stability and synchronization criteria of linearly coupled gyroscopy", Nonlinear Dynamics and Systems Theory, 13(3), 2013.

* cited by examiner $\check{n} = 1$
$\check{m} = 6$
$T_1 = T$
$\alpha_{1n} = \alpha_{1n-1} + \pi/3$ $\check{n} = 2$
$\check{m} = $ func.
$T_1 = 0 \quad T_2 = T$

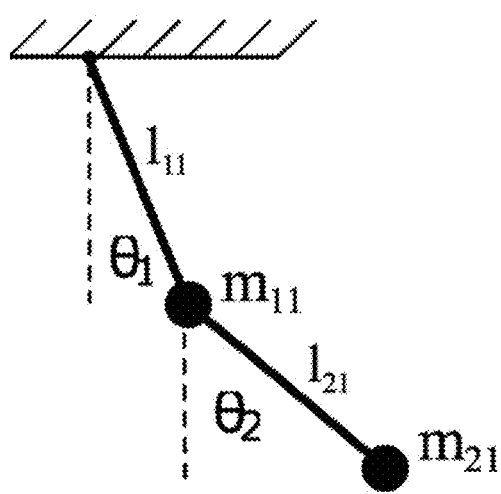
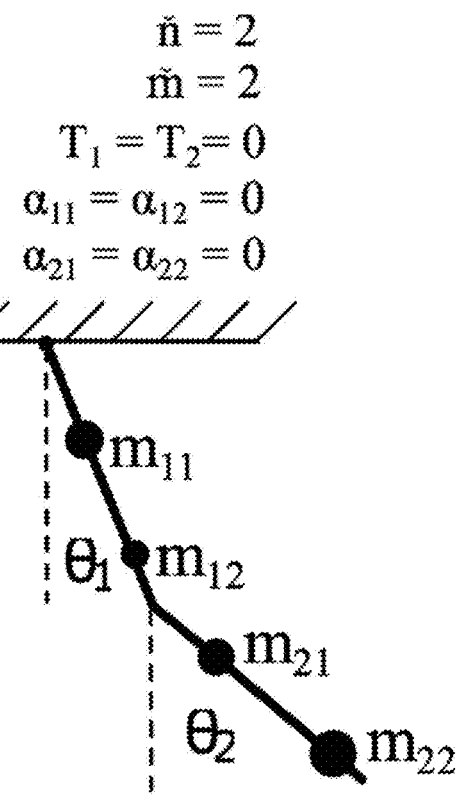
FIG. 6A  FIG. 6B

SYSTEMS AND METHODS FOR SYNCHRONIZING THE KINEMATICS OF UNCOUPLED, DISSIMILAR ROTATIONAL SYSTEMS

CROSS-REFERENCE TO RELATED APPLICATION

This application claims priority to U.S. Provisional Application Ser. No. 62/003,738, filed May 28, 2014, which is hereby incorporated by reference herein in its entirety.

BACKGROUND

Kinematic synchronization of systems is the matching of motion between two moving systems. The synchronization of any two rotational systems can be as simple as placing a joining spring or damper between the systems or may require sophisticated controllers. This form of coupled synchronization of systems has been studied since the 15th century. Unfortunately, it requires the systems to be physically connected. It would be desirable to be able to synchronize the motion of two dissimilar rotational systems without coupling them together physically or through controlled actuation.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 2A is a seesaw/rotor model, FIG. 2B is a double-pendulum model, FIG. 2C is a cam model, and FIG. 2D is model having a continuous mass distribution along rotating members.

FIG. 6A is a diagram of a double-link pendulum model having a single point mass on each link.

FIG. 6B is a diagram of a double-link pendulum model having two point masses on each link.

DETAILED DESCRIPTION

Figure 1:
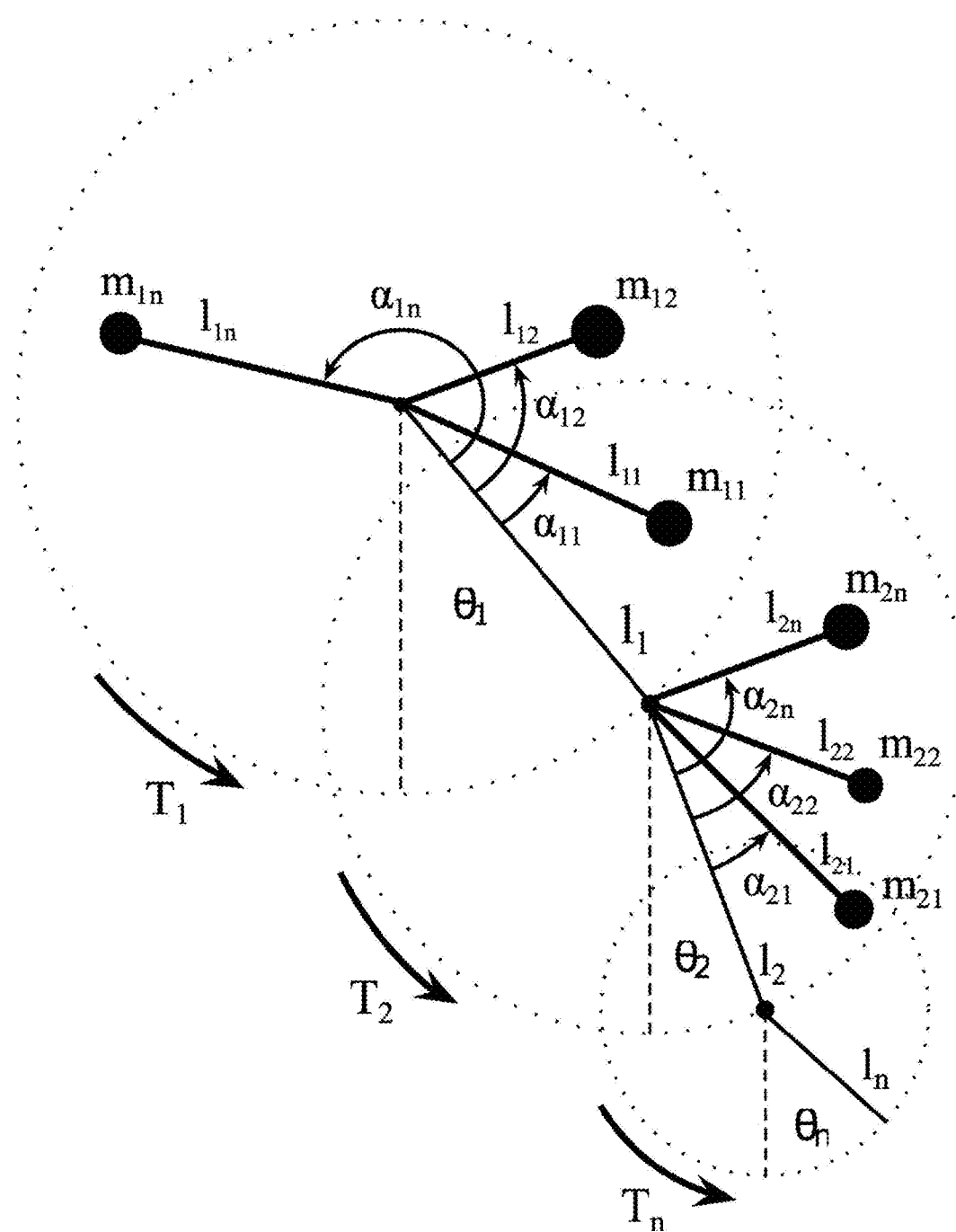
FIG. 1 is a diagram of a general rotational system model.
Figure 2A:
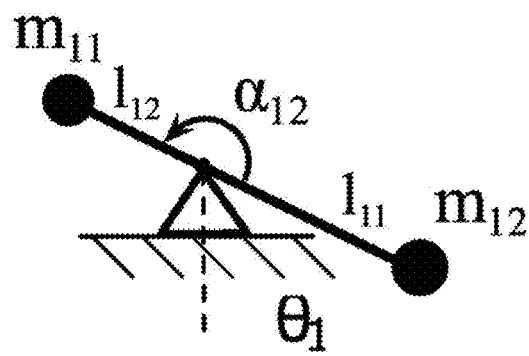
FIGS. 2A-2D are diagrams of rotational system models that represent various configurations for rotating systems with any number of joints.
Figure 2B:
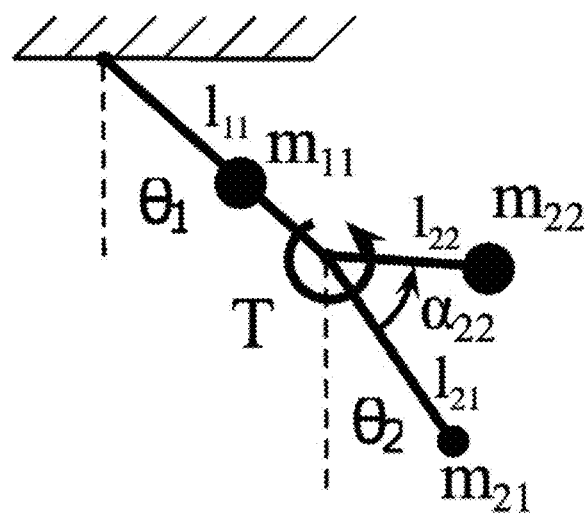
Figure 2C:
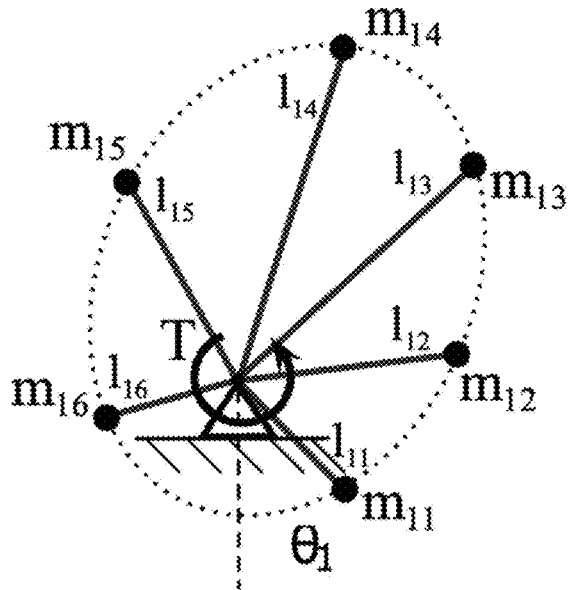
Figure 2D:
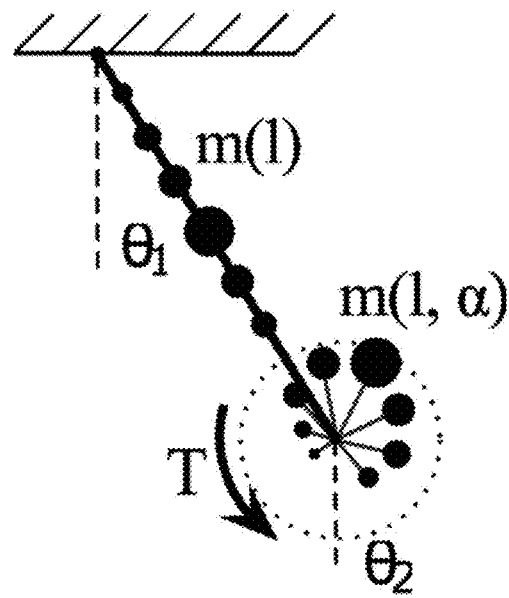

As described above, it would be desirable to be able to synchronize the motion of two dissimilar rotational systems without coupling them together. Described herein is a kinematic matching technique that can be used to passively synchronize two physically dissimilar rotational systems. The technique is generalizable and can be used to describe and match the kinematics of any open-ended rotational system chain, such as rotors, cams, or pendulums. As will be apparent from the discussion that follows, the technique has implications for the modeling of system dynamics, the study of swinging limbs in humans, animals, and robots, and in prosthesis design.

In the following disclosure, various specific embodiments are described. It is to be understood that those embodiments are example implementations of the disclosed inventions and that alternative embodiments are possible. All such embodiments are intended to fall within the scope of this disclosure.

Described herein is a kinematic matching technique that can be used to synchronize two dissimilar rotational systems without coupling the systems together. The technique enables two separate and dissimilar systems to generate the same motion without any system coupling or control law. The technique is validated herein by applying it to two open-ended rotational kinematic chains: single- and double-link pendulums with different masses and mass distributions. Even though double-link pendulums are nonlinear chaotic systems that are sensitive to changes in parameters, the disclosed matching technique enables the same generated motion on dissimilar double-link pendulums.

The practical application of the kinematic matching technique is the flexibility in mechanical design as one is able to describe the same kinematics with a variety of parameters (i.e., masses and mass distributions). In essence, one can decouple the mass and the first and second moments of inertia so systems with dissimilar masses and mass distributions will have the same motion. For example, the motion of a double-link pendulum modeled as two links with one mass per link can only be described by one unique combination of masses and mass locations along the links. However, having two masses per link allows the kinematics to be described with an infinite number of distinct systems that all have the same motion. In fact, the minimum number of masses per rotational link to describe any arbitrary rotational kinematics is two masses, yet many models only include one mass. Using only one mass per link inherently couples the moments of inertia so that any change in the location of the mass necessarily affects both the first and second moments of inertia.

The disclosed kinematic matching technique can be used to simplify complicated kinematics problems that yield identical results. For example, the rotation of a fan blade can be represented with two masses distributed as specified using the technique instead of finding detailed masses, mass distributions, or moments of inertias of the continuous system. In turn, it is possible to use this matching technique to design a second, completely different rotational system that moves identically. Such a method can be useful in, for example, the simplification of a kinematic system model, in the manipulation of human or robotic limb movement, and in prosthesis design. The only requirements for passive kinematic synchronization are identical degrees of freedom, initial conditions, and torques applied to the systems. These same requirements are also needed to cause two identical systems to have the same motion.

The kinematic synchronization of two or more coupled mechanical systems has been extensively studied since the 17th century. More recent studies include the synchronization of coupled nonlinear oscillators, analysis of coupled multi-pendulum systems, and synchronization of double pendulums under the effects of external forces. Along with the rise of faster computing power has come the ability to actively synchronize coupled mechanical systems with linear, nonlinear, passivity-based, or active control laws. There are hundreds of publications that demonstrate such control laws. Some of these publications are focused on controlled motion synchronization for dual-cylinder electrohydraulic lift systems, inverted pendulum systems, and chaotic systems.

Passive kinematic synchronization of uncoupled systems has been studied significantly less. Despite this fact, such synchronization has practical implications for locomotion robotics, lower limb gait analysis, and prosthetics. For instance, an individual's gait can largely be modeled as two inverted pendulums (left and right step) rotating about the stance foot and progressing down a decline with gravity as the only source of energy. Such models are called passive dynamic walkers (PDWs) and have been shown to predict certain aspects of human gait dynamics. A brute force search through a numerical PDW model has been used to show that asymmetric limbs can have symmetric kinematics and that moving a prosthetic knee joint lower while lowering the prosthetic mass can result in a spatially symmetric gait. Others have examined symmetry from the other point of view by finding symmetric PDW parameters that yielded asymmetric kinematics. A motion matching technique for PDWs and individuals can be helpful in the design and implementation of devices and methods that either even out gait asymmetries or intentionally exaggerate gait asymmetries for purposes of rehabilitation. These gait asymmetries can also arise from the asymmetric size and weight of a prosthetic limb.

The equations used to derive the kinematics of a two-dimensional general rotational system will now be discussed, and a method for synchronizing two or more uncoupled dissimilar rotational systems with the same degrees of freedom, initial conditions, and torque input will be derived. The discussion begins with derivation of a general rotational system with $\breve{n}$ degrees of freedom and $\breve{m}$ masses per degree of freedom. Note that m symbolizes each individual mass whereas $\breve{m}$ symbolizes the total number of masses. This generalized model is shown in FIG. 1, and can be described using Lagrangian mechanics where the Lagrangian is defined as the difference of kinetic and potential energy.

$$L(\theta,\dot{\theta},t)=K(\theta,\dot{\theta},t)-U(\theta,t) \quad \text{[Equation 1]}$$

To find the equation of motion, the Euler-Lagrange expression is applied.

$$\frac{d}{dt}\left(\frac{\partial L(\theta,\dot{\theta},t)}{\partial \dot{\theta}_{1,2...\breve{n}}}\right) = \frac{\partial L(\theta,\dot{\theta},t)}{\partial \theta_{1,2...\breve{n}}} \quad \text{[Equation 2]}$$

Equation 2 produces $\breve{n}$ equations. After differentiating and collecting coefficients, the equations of motion of this general rotational system is a set of first order nonlinear ordinary differential equation $$[M]\ddot{\Theta}+[N]\dot{\Theta}^2+[G]=[T] \quad \text{[Equation 3]}$$

where the coefficient matrices [M], [N], and [G] are given in Equations (4), (7), and (8), respectively.

$$[M]_{sym}^{\breve{n},\breve{n}} = \begin{bmatrix} M_{1,1} & M_{1,2}\cos(\theta_1-\theta_2) & \cdots & M_{1,j}\cos(\theta_1-\theta_j) \\ M_{1,2}\cos(\theta_1-\theta_2) & M_{2,2} & & \vdots \\ \vdots & & \ddots & M_{i-1,j}\cos(\theta_{i-1}-\theta_j) \\ M_{1,j}\cos(\theta_1-\theta_j) & \cdots & & M_{i,i} \end{bmatrix} \quad \text{[Equation 4]}$$

where each of the coefficients on the diagonal are given by $$M_{i,i} = \sum_{p=1}^{\breve{m}} l_{i,p}^2 m_{i,p} + l_i^2 \sum_{q=i+1}^{\breve{n}} \sum_{p=1}^{\breve{m}} m_{q,p} \quad \text{[Equation 5]}$$

and the remaining non-diagonal coefficients are given by $$M_{i,j} = l_i \left[ \sum_{p=1}^{\breve{m}} l_{j,p} m_{j,p} + \begin{cases} l_j \sum_{q=j+1}^{\breve{n}} \sum_{p=1}^{\breve{m}} m_{q,p} & j < \breve{n} \\ 0 & j \geq \breve{n} \end{cases} \right] \quad \text{[Equation 6]}$$

$$[N]^{\check{n},\check{n}} = \begin{bmatrix} 0 & M_{1,2}\sin(\theta_1 - \theta_2) & \cdots & M_{1,j}\sin(\theta_1 - \theta_j) \\ -M_{1,2}\sin(\theta_1 - \theta_2) & 0 & & \vdots \\ \vdots & & \ddots & M_{i-1,j}\sin(\theta_{i-1} - \theta_j) \\ -M_{1,j}\sin(\theta_1 - \theta_j) & \cdots & & 0 \end{bmatrix} \quad \text{[Equation 7]}$$

$$[G]^{\check{n}} = \begin{bmatrix} \sum_{p=1}^{\check{m}} l_{1,p} m_{1,p} \sin(\alpha_{1,p} + \theta_1) + \left( l_1 \sum_{q=2}^{\check{n}} \sum_{p=1}^{\check{m}} m_{q,p} \right) \sin(\theta_1) \\ \sum_{p=1}^{\check{m}} l_{i,p} m_{i,p} \sin(\alpha_{i,p} + \theta_i) + \left( l_1 \sum_{q=i+1}^{\check{n}} \sum_{p=1}^{\check{m}} m_{q,p} \right) \sin(\theta_i) \\ \sum_{p=1}^{\check{m}} l_{\check{n},p} m_{\check{n},p} \sin(\theta_{\check{n},p} + \theta_{\check{n}}) \end{bmatrix} g \quad \text{[Equation 8]}$$

These are the coefficient matrices for the equations of motion of a general rotational system model with ň degrees of freedom and m̃ masses per degree of freedom. The [M] matrix is a symmetric matrix, while the [N] matrix is a negatively mirrored matrix with a zero diagonal.

Note that the coefficients in Equations 5 and 6 are all unique matrix components in the [N] matrix that all appear in the [M] matrix. Also note that the last row of [G] (i=ň) is different since there are no masses from links further down the chain. Masses (m̃) and mass distributions (l) are shown in FIG. 1.

Equation 3 can model any degree of rotational system or rotational system links. That is, Equation 3 can represent any rotational system with any number of joints. Degrees of freedom (links), masses, and mass distributions within each link can be easily modified to create models for such systems as shown in FIGS. 2A-2D. These modified models can represent rotors, pendulums, cams, or rotational kinematic systems and open kinematic chains. Note that the coefficient [T] on the right side of Equation 3 can include any torque created by actuators, breaks, dampers, or any other source of linear or non-linear torque that is a function of angular position, angular velocity, or angular acceleration.

Given the same applied torque input and initial conditions, two or more arbitrary systems with the same degrees of freedom will exactly match if all three coefficient matrices [M], [N], and [G] in Equation 3 are matched between systems. Since only the values of the coefficient matrices [M], [N], and [G] in Equation 3 determine the behavior of the systems, the specific masses and mass distribution do not have to match between them. This enables two or more systems with dissimilar mass and mass distribution parameters to kinematically behave identically. For instance, assuming identical torque input and initial conditions, a swinging single link pendulum with one mass can be designed to swing identically to another single link pendulum of two or more masses. This concept allows for the first and second moments of inertia to be decoupled and greater design flexibility is obtained.

For synchronization between two dissimilar and uncoupled rotational systems, matrix [M] of the first system has to match matrix [M] of the second system, matrix [N] of the first system has to match matrix [N] of the second system, and matrix [G] of the first system has to match matrix [G] of the second system. These coefficient matrices in Equation 3 are composed of individual matrix terms/entries that, when combined, equal that whole coefficient matrix. These unique terms that appear inside the coefficient matrices [M], [N], and [G] in Equation 3 can be referred to as kinematically matched coefficients (KMCs). Therefore, if two dissimilar rotational systems are to be made to have the same kinematic behavior, the KMCs of each system can be equated. Examples of this are described below. The number of KMCs that have to be matched between kinematically synchronized rotational systems is identified in Table 1. As can be appreciated from that table, to synchronize the dynamics of a pair of one degree-of-freedom rotational systems, two KMCs must be matched, while for a pair of three degree-of-freedom rotational systems, nine KMCs must be matched.

TABLE 1

Number of Kinematically Matched Coefficients For Synchronized Uncoupled Motion between Two or More Systems

| System Degree of Freedom (ň) | Number of KMCs |
| --- | --- |
| 1 | 2 |
| 2 | 5 |
| 3 | 9 |
| . | . |
| . | . |
| . | . |
| ň | $KMC_{\check{n}-1} + (\check{n} + 1)$ |

It is noted that Equation 3 includes any nonconservative forces (e.g., friction) in the term on the right hand side, [T]. If such forces are added to be matched between systems, however, it would also produce another coefficient matrix that would similarly need to be matched between systems in order to produce matching kinematics. This additional matrix that can potentially be matched from applied torques has intentionally been excluded since it can represent any type of applied torque which includes anything from simple applied motor torque to complex non-linear friction models.

Figure 3A:
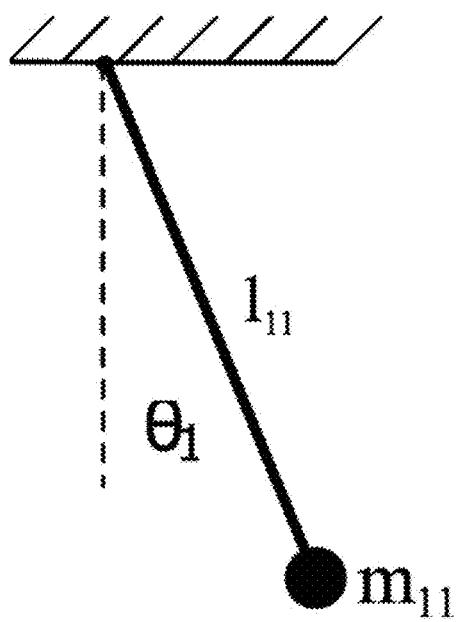
FIG. 3A is a diagram of a single-link pendulum model having a single point mass.
Figure 3B:
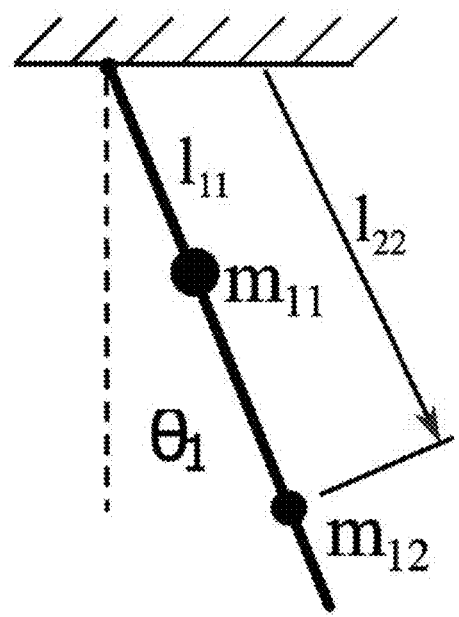
FIG. 3B is a diagram of a single-link pendulum model having two point masses.

A general method was derived above that enables two or more dissimilar rotational systems to be kinematically matched. The validity of this method was experimentally demonstrated. In one experiment, the kinematics of three simplified versions of the general rotational model, which are all passive single link pendulums, were synchronized. One of the experimental pendulums was a single mass (m̃=1), single link (ň=1) pendulum (see FIG. 3A) and the other two pendulums were double mass (m̃=2), single link (ň=1) pendulums (see FIG. 3B). Although more masses could be utilized to match the motion of this single link pendulum, two masses are sufficient to describe any number of masses and mass distributions. The parameters of these three dissimilar single link pendulums are shown in Table 2. Since a single link pendulum is one degree of freedom, only two KMCs (see Table 1) had to be matched between systems ($M_{1,1}$=33,600 g-cm² and $G_1$=1,260 g-cm).

TABLE 2

Single Pendulum ($\check{n} = 1$) System Synchronization Coefficient Equations and System Experimental Parameters

| | Coefficient Index | Coefficient Value | System 1 ($\check{m} = 1$) | System 2 ($\check{m} = 1$) | System 3 ($\check{m} = 1$) |
|---|---|---|---|---|---|
| KMCs | $M_{1,1}$ | 33,600 g-cm² | $m_{11}l_{11}^2$ | | $m_{11}l_{11}^2 + m_{12}l_{12}^2$ |
| | $G_1$ | 1,260 g-cm | $m_{11}l_{11}$ | | $m_{11}l_{11} + m_{12}l_{12}$ |
| Masses (g) | | | $m_{11} = 47.3$ | $m_{11} = 35.0$ | $m_{11} = 49.01$ |
| | | | | $m_{12} = 21.0$ | $m_{12} = 31.8$ |
| Lengths (cm) | | | $l_{11} = 26.7$ | $l_{11} = 15.0$ | $l_{11} = 5.0$ |
| | | | | $l_{12} = 35.0$ | $l_{12} = 31.9$ |

The three dissimilar single link pendulum systems were constructed from rigid foam board that was light (1.125 g per link) relative to the pendulum masses. Mass and mass distributions were calculated using the KMCs in Equations 4, 7, and 8. Lead weights were used as pendulum masses and attached to the link at appropriate positions. The mass values listed in Table 2 were rounded to whole grams for the experimental pendulums. To ensure precise link dimensions, each pendulum was cut with a 60 Watt laser cutter (Universal Systems VLS4.60).

The links were attached to a short and rigid 0.375 in (0.9525 cm) aluminum rod using a precision steel ball bearing to reduce friction. To minimize variability due to friction (negative torque), the exact same bearing was used for each system. Each pendulum system was dropped from the same initial position with an adjustable spring loaded release mechanism. This complete setup can be seen in FIG. 4.

The pendulums were video recorded at 50 frames/second (50 Hz). Link angular position was interpreted with Matlab®, which was used to load video frames and identify each link's distinct color while in motion.

Five videos of each pendulum were recorded (15 total). The recorded angular positions were averaged and filtered using a low pass 2nd order Butterworth filter at 6 Hz. This angular position data is presented in FIG. 5 and compared with ideal predicted model behavior. Modeled systems had the same masses and mass distribution as measured systems. As predicted, all three ideal modeled systems had the same temporal kinematics and overlap in FIG. 5. Spectral analysis showed the same frequency peak between all measured systems, while all three modeled systems peaked 0.06 Hz below the measured system peaks.

While the recorded systems were affected by nonconservative forces, such as air resistance and bearing friction, all three dissimilar pendulums matched kinematically. Their slight difference in amplitude can be explained by the variable mass and mass distribution in the pendulums that leads to variable weight and centripetal forces on the bearing, which in turn increases friction. Similarly, the effect of the friction torque is affected by the inertia of the system. Although the kinematics were matched, the kinetics in these dissimilar systems does not match; the different masses will generate different forces. Despite these small effects, all three physically dissimilar pendulums had a frequency of 0:88±0:04 Hz.

Figure 5:
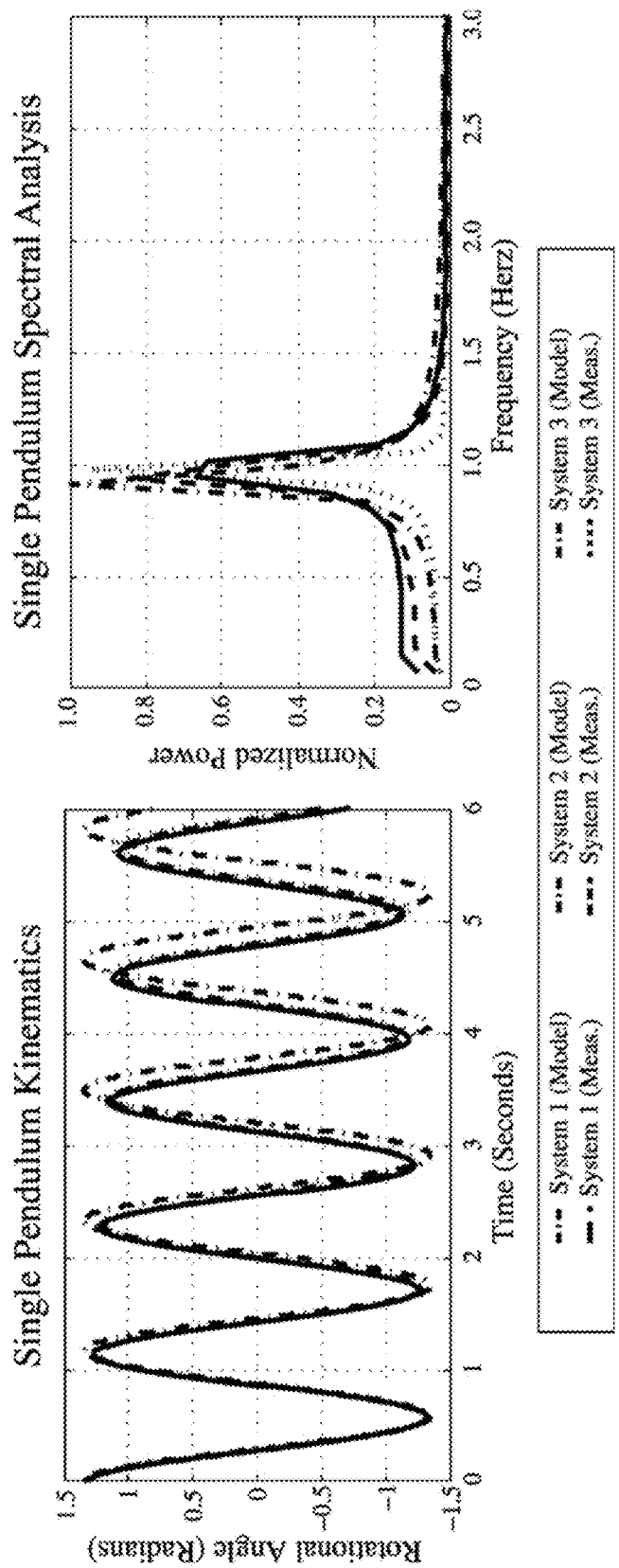
FIG. 5 includes graphs that plot experimental rotational link position and spectral analysis for a single-link pendulum ($\dot{n}=1$).

When comparing the collected and model data, the effects of damping become distinct. As a result, the amplitude and period decrease over time for the actual systems, as shown in FIG. 5. As previously explained, the model derivation did not include a damping coefficient, thus its effect on motion was not predicted. Despite this difference, the model and all three physically dissimilar pendulums had very similar motion.

Next, two dissimilar two degree-of-freedom systems (passive double pendulums) were also synchronized using the kinematic matching technique. The double pendulum models are depicted in FIGS. 6A and 6B and the KMCs are shown in Table 3.

TABLE 3

Double Pendulum ($\check{n} = 2$) Synchronization Coefficient Equations and Experimental System Parameters

| | Coefficient Index | Coefficient Value | System 1 ($\check{m} = 2$) | System 2 ($\check{m} = 2$) |
|---|---|---|---|---|
| KMCs | $M_{1,1}$ | 28,175 g-cm² | $l_{11}^2 m_{11} + l_{12}^2 m_{12} + l_1^2(m_{21} + m_{22})$ | |
| | $M_{1,2}$ | 23,8000 g-cm² | $l_1(l_{21}m_{21} + l_{22}m_{22})$ | |
| | $M_{2,2}$ | 32,900 g-cm² | $l_{21}^2 m_{21} + l_{22}^2 m_{22}$ | |
| | $G_1$ | 1,715 g-cm | $l_{11}m_{11} + l_{12}m_{12} + l_1(m_{21} + m_{22})$ | |
| | $G_2$ | 1,190 g-cm | $l_{21}m_{21} + l_{22}m_{22}$ | |
| Masses (g) | | | $m_{11} = 5.0$ | $m_{11} = 52.6$ |
| | | | $m_{12} = 35.0$ | $m_{12} = 29.1$ |
| | | | $m_{21} = 14.0$ | $m_{21} = 23.0$ |
| | | | $m_{22} = 35.0$ | $m_{22} = 28.0$ |
| Lengths (cm) | | | $l_1 = 20.0$ | $l_1 = 20$ |
| | | | $l_{11} = 7.0$ | $l_{11} = 5.0$ |
| | | | $l_{12} = 14.0$ | $l_{12} = 15.0$ |
| | | | $l_{21} = 10.0$ | $l_{21} = 12.4$ |
| | | | $l_{22} = 30.0$ | $l_{22} = 32.4$ |

The traditional double pendulum is modeled in FIG. 6A. This model, however, is impractical from a design perspective considering that the pivot point between the upper and lower link is exactly where the mass is placed and the link is massless. Hence, design flexibility was added by utilizing two masses per link for this comparison, as shown in FIG. 6B.

Two double pendulums were created using the same fabrication technique and material as the single pendulum experiment described above. An additional small ball bearing was placed at the pivot point between the upper and lower link with a 0.25 in (6.25 mm) wooden pin. Both small bearing and pin had a combined weight less than 2 grams.

Figure 4:
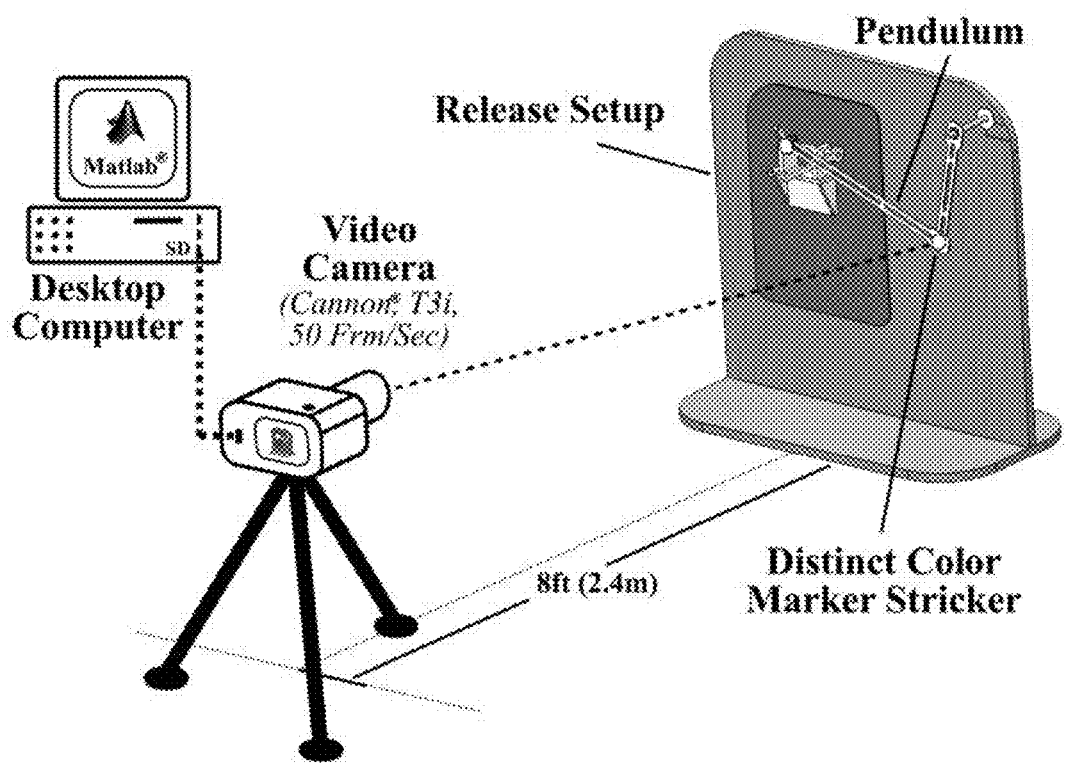
FIG. 4 is a diagram of a release mechanism used in pendulum experiments.

The links were attached to the same aluminum rod and ball bearing, and were released with the same release mechanism shown in FIG. 4. Specific colors were placed on each link to track their angular positions. The double pendulum nonlinear motion was recorded at 50 frames/second (50 Hz).

Figure 7:
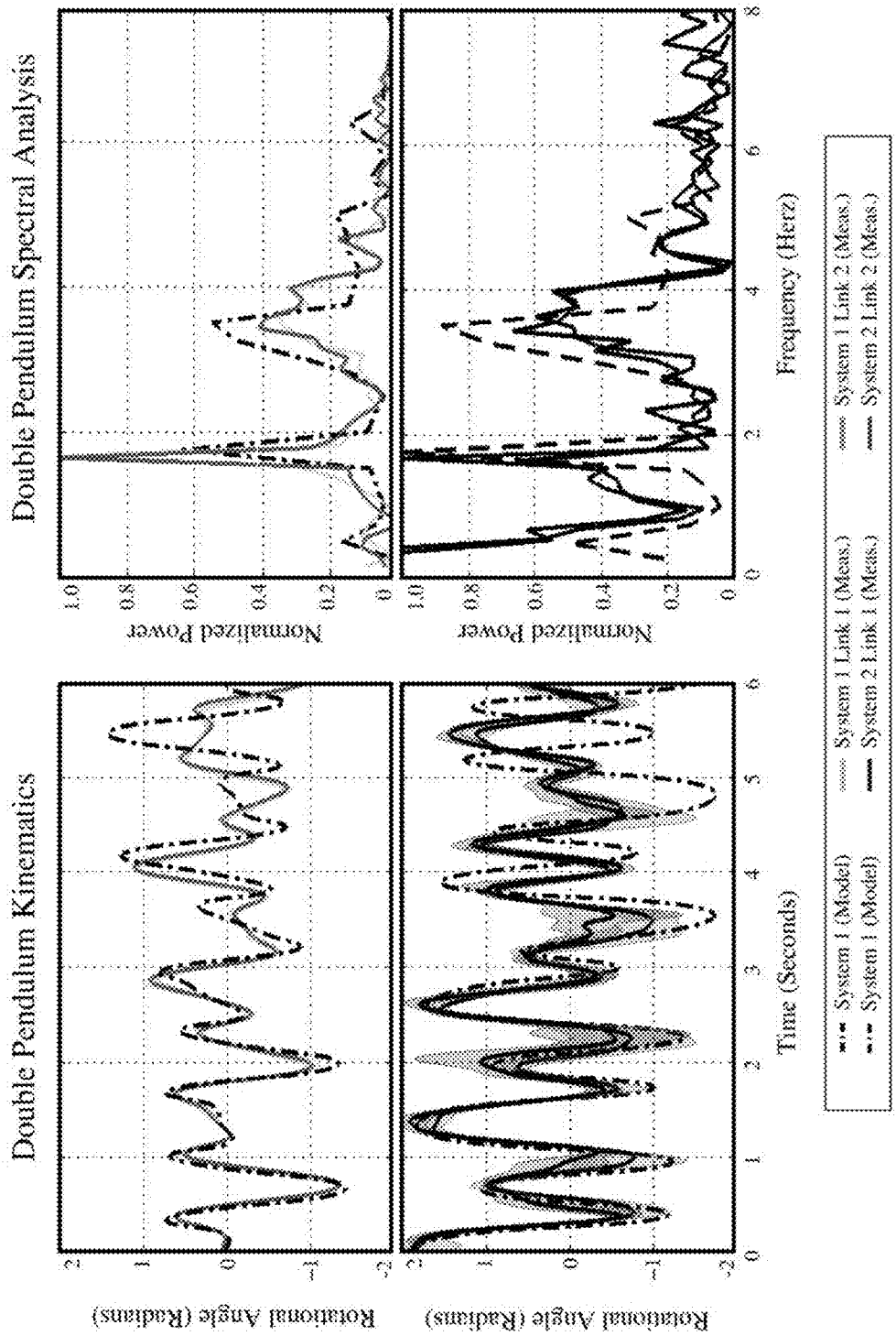
FIG. 7 includes graphs that plot experimental rotational link position and spectral analysis for a double-link pendulum ($\dot{n}=2$).
Figure 8:
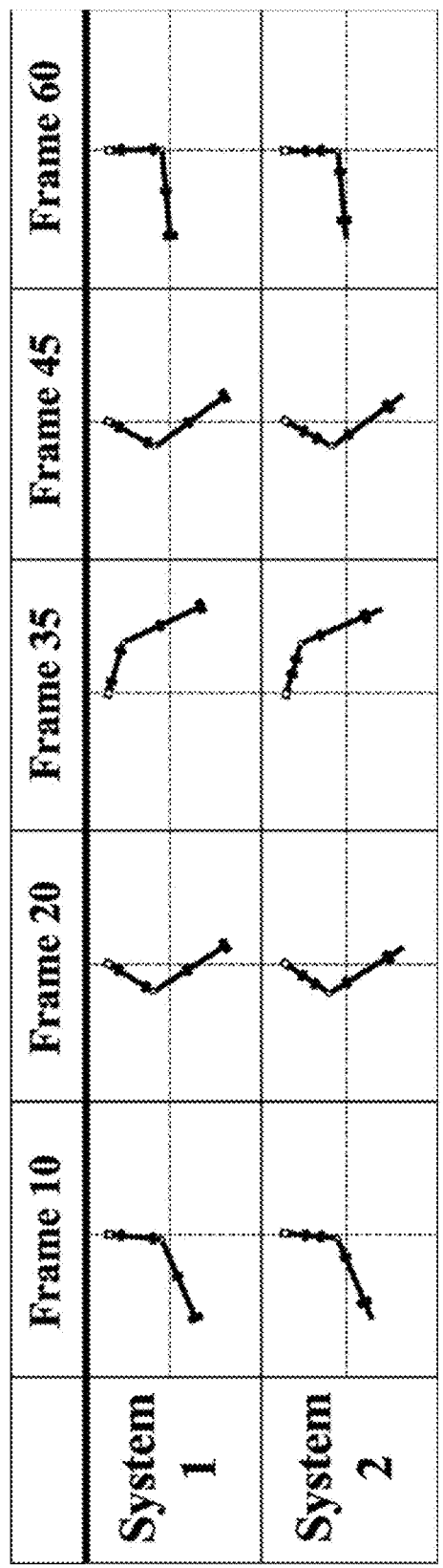
FIG. 8 includes captured images of two dissimilar double pendulums ($\dot{n}=2$) moving in synchronization as they are released with identical initial conditions.

As before, each pendulum's angular kinematics were recorded five times (10 total), averaged, and filtered with a 2nd order Butterworth filter at 6 Hz. The results of these angular positions are illustrated in FIG. 7 and compared with the ideal predicted systems. The motion for both link 1 (upper link) and link 2 (lower link) was in agreement with model conditions through around 4 seconds, but were in good agreement between experimental measurements throughout the whole trial, which was 12 seconds. This movement of the two dissimilar systems can be seen in FIG. 8. All collected data deviates less for link 1 than link 2, which can be explained by the more chaotic movement of the lower link and also because of more variability due to friction in the additional middle pivot. In summary, the two dissimilar chaotic systems have been demonstrated as having the same motion by kinematically matching the two systems.

Figure 9:
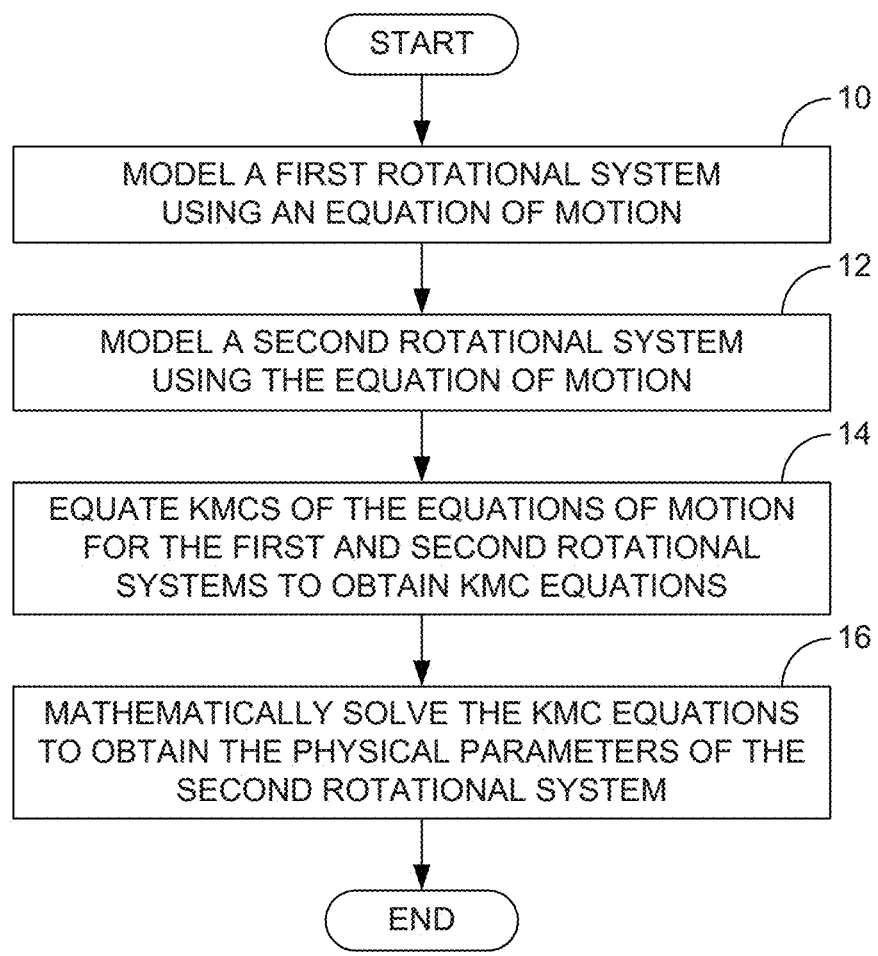
FIG. 9 is a flow diagram of a method for synchronizing the kinematics of two dissimilar rotational systems.

FIG. 9 is a flow diagram the summarizes the above-described kinematic synchronization technique. Using this technique, the kinematics of a one rotational system can be matched to the kinematics of an uncoupled, dissimilar rotational system. The first (reference) system, System A, can be an existing system while the second system, System B, can either be another existing system or a system that is to be designed and constructed.

Beginning with block 10 of FIG. 9, a first rotational system, System A, is modeled using an equation of motion that defines the kinematics of the system. This equation of motion can be that of Equation 3 above. Referring next to block 12, a second, dissimilar rotational system, System B, is modeled using the equation of motion.

After both of the rotational systems have been modeled, the KMCs of the equations of motion for the first and second systems are equated to obtain KMC equations, as indicated in block 14. Once the KMC equations have been obtained, they can be mathematically solved to obtain the physical parameters of the second rotational system (System B), as indicated in block 16. With these parameters, the second rotational system can be designed and constructed, if desired.

Figure 10:
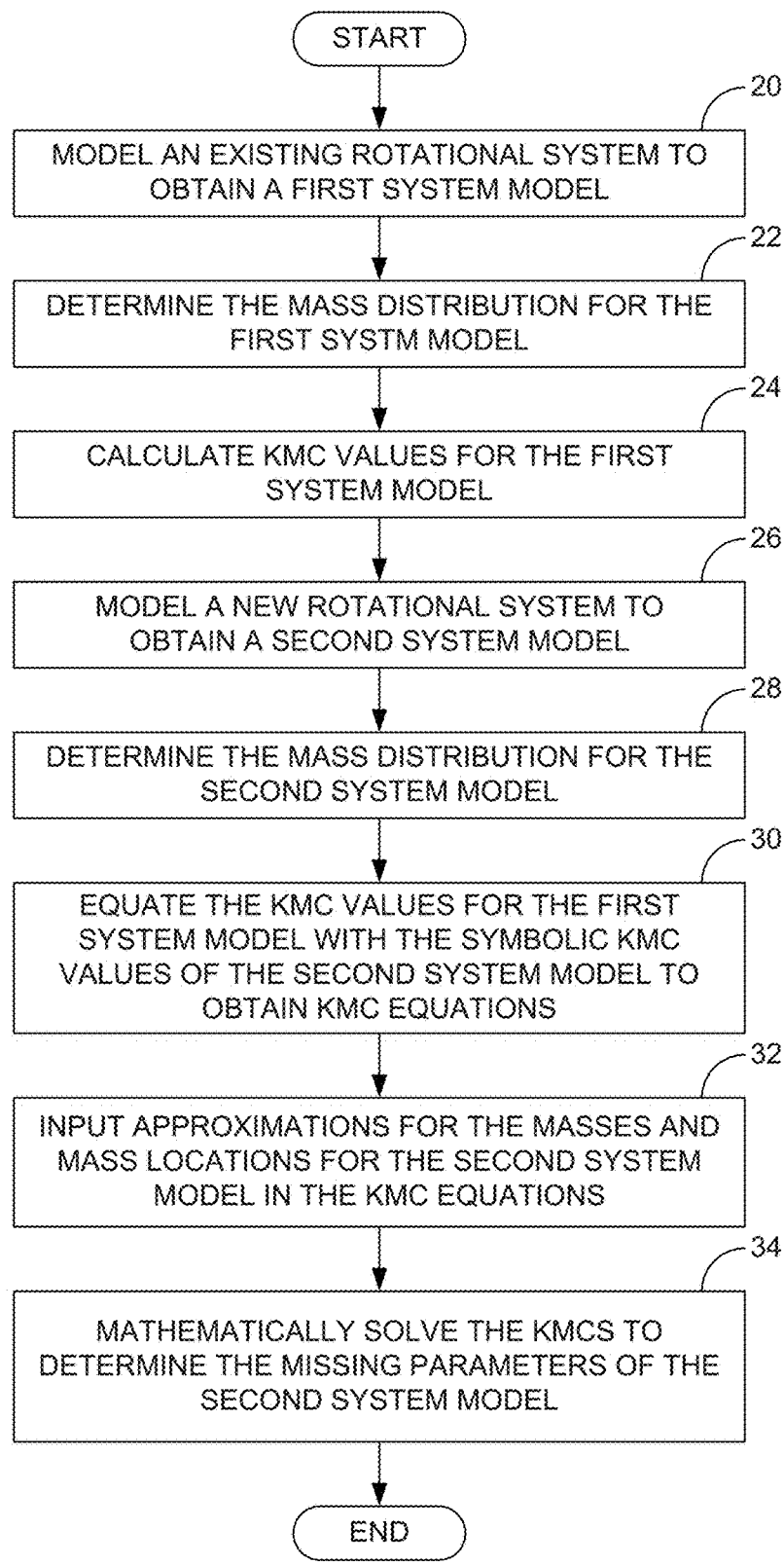
FIG. 10 is a flow diagram of a method for designing a new rotational system having the same kinematics of an existing rotational system.
Figure 11:
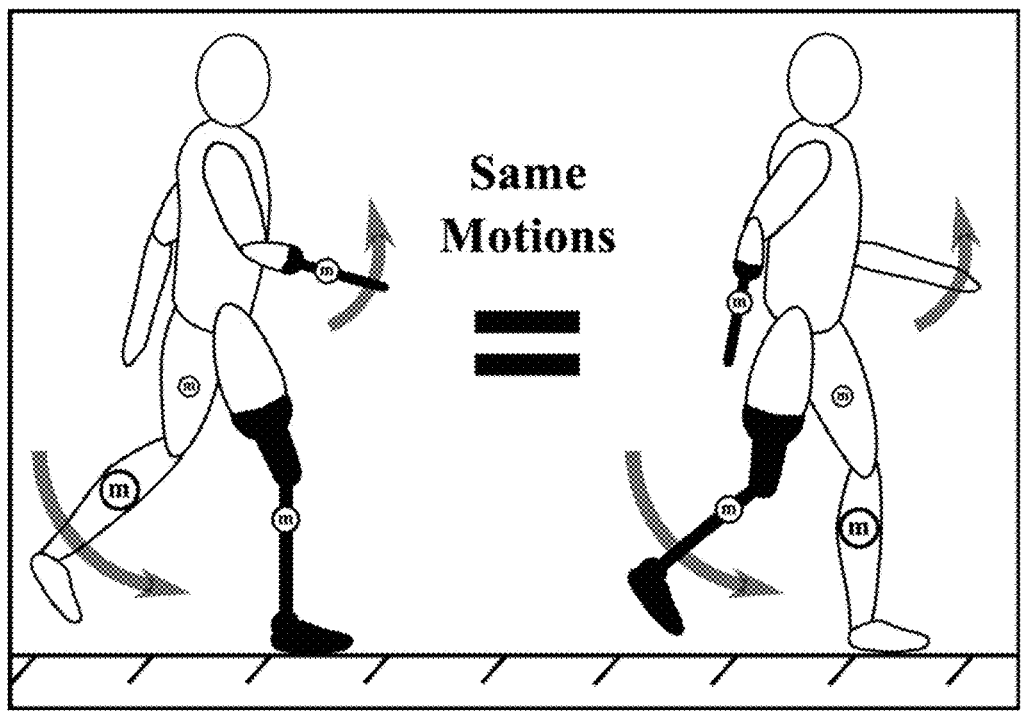
FIG. 11 is a diagram that illustrates kinematic synchronization between an intact leg and a leg prosthesis to be modified.

FIG. 10 is another flow diagram that describes a method for synchronizing the kinematics of two rotational systems. This method, however, addresses a specific kinematic matching example. Specifically, FIG. 10 describes a method for designing a new rotational system (System B) that is kinematically synchronized with an existing rotational system (System A). One example of such a situation is that of designing a leg prosthesis for an amputee. In that situation, the amputee's intact leg can be the existing rotational system and the prosthesis that is to be designed to replace the amputee's missing leg can be the second rotational system. By matching the kinematics of the two systems, the prosthesis can be designed in a manner that facilitates an even walking gait. This is schematically illustrated in FIG. 11.

Figure 12:
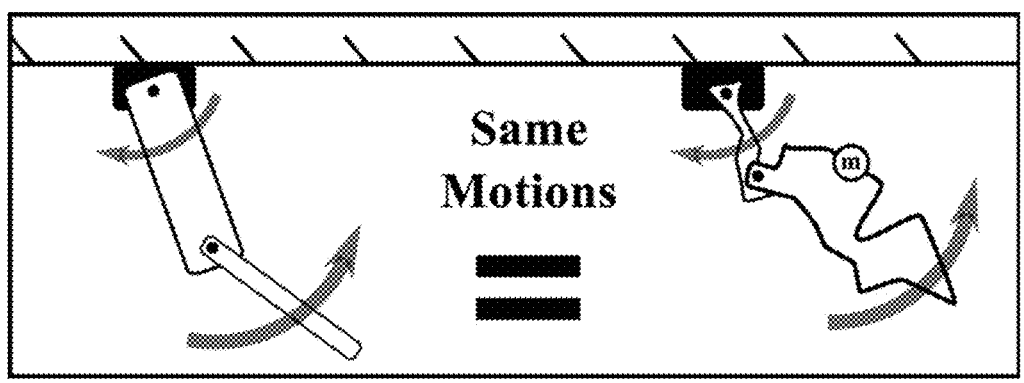
FIG. 12 is a diagram that illustrates kinematic synchronization between two dissimilar pendulums.

Beginning with block 20 of FIG. 10, an existing rotational system (System A) is modeled to obtain a first system model (Model A). In some embodiments, the existing rotational system can be modeled as a pendulum. For example, if the task involves designing a prosthesis for a missing leg as described above, the existing leg could be modeled as a one-link pendulum ($\check{n}=1$) that represents the entire leg or a two-link pendulum ($\check{n}=2$) having a first link that represents the upper leg and a second link that is joined to the first link that represents the lower leg, with the joint representing the knee. Notably, the existing rotational system does not need to be modeled as a conventional pendulum. For example, the links of the system do not need to be linear members and the masses provided on the links do not need to be positioned along the central longitudinal axis of the links. This is illustrated in FIG. 12, which shows a conventional pendulum on the left and a non-conventional pendulum on the right. In some embodiments, the existing rotational system, such as a leg, can be modeled as a single link having a single point mass ($\check{n}=1$) for purposes of simplicity. In other embodiments, the system can be modeled with multiple links each having one or more masses. Notably, if multiple links are used, each link must have the same number of masses, even if one or more of these masses are set to zero.

Referring next to block 22, the mass distribution for the first system model can be determined. This step involves identifying point masses and their locations on their respective links. These parameters can be determined by measuring the existing rotational system. For example, if the existing rotational system is the intact leg and the leg is modeled as a single link having a single mass, the mass distribution can be determined by measuring the moment of inertia of the leg. As the moment of inertia is equal to the point mass multiplied by the square of its distance along the link (i.e., length), once the moment of inertia is known, the mass or length can be determined by selecting a value for the other of the mass or length and solving for the missing value.

With reference next to block 24, the KMC values can be calculated for the first system model. These values can be calculated using Equations 4, 7, and 8. In particular, one can input the physical parameters of the mass distribution determined in block 22 to obtain the various KMC values. In keeping with the above example, in which an intact leg has been modeled as a single link having a single mass, the first system model has one degree of freedom and, as indicated in Table 2, there are two KMCs: M and G. As an example, the computed values could be:

$$M_{1,1}{}^A = 30{,}000 \text{ g-cm}^2$$

$$G_1{}^A = 1{,}000 \text{ g-cm}$$

With reference next to block 26, a new rotational system (System B) to be designed can be modeled to obtain a second system model (Model B). The second system model must have the same number of degrees of freedom as the first system model. Therefore, in keeping with the above example, if the first rotational system was modeled as a one degree-of-freedom system, the second rotational system must be modeled as a one degree-of-freedom system. Once the second system model has been created, its mass distribution can be determined, as indicated in block 28. As described below, not all of the parameters for the mass distribution, including masses and lengths, need net be known or approximated. In fact, some of these parameters are what are being determined through the kinematic synchronization process. It is noted that the links of the second rotational system must have at least two masses each and, as with the first system model, each link must have the same number of masses.

Turning to block 30, the KMC values of the first system model are equated with the symbolic KMCs of the second system model to obtain KMC equations. As an example:

$$M_{1,1} = 30{,}000 \text{ g-cm}^2 = m_{11}{}^B (l_{11}{}^B)^2 + m_{12}{}^B (l_{12}{}^B)^2$$

$$G_1 = 1{,}000 \text{ g-cm} = m_{11}{}^B l_{11}{}^B + m_{12}{}^B l_{12}{}^B$$

At this point, approximations for the masses and lengths for the second system model can be input into the KMC equations, as indicated in block 32. In doing this, the number of unknown variables are kept equal to the number of KMCs. Therefore, if there are two KMCs as in the above example, two of the masses, two of the lengths, or one of the masses and one of the lengths are left as variables to be solved for and approximations are provided for the other masses/lengths. In some embodiments, the approximations are selected based upon the design constraints for the second rotational system. For example, if the second rotational system is to be a leg prosthesis, the approximations input into the KMC equations can be a mass that is positive and a length that is positive but no longer than the length of the amputee's intact leg. Below is an example in which a mass, $m_{11}{}^B$, was selected to be 35 g and the length $l_{12}{}^B$ was selected to be 31.9 cm:

$$M_{11} = 30{,}000 \text{ g-cm}^2 = (35 \text{ g})(l_{11}{}^B)^2 + m_{12}{}^B (31.9 \text{ cm})^2$$

$$G_1 = 1{,}000 \text{ g-cm} = (35 \text{ g}) l_{11}{}^B + m_{12}{}^B (31.9 \text{ cm})$$

Once the mass and length approximations have been input into the KMC equations, the equations can be mathematically solved to determine the missing parameters, as indicated in block 34. This can be accomplished, for example, by solving the equations as a system of linear equations or by using a suitable mathematical optimization method. In keeping with the above example, the missing parameters can be calculated to be:

$$m_{12}{}^B = 29.37 \text{ g}$$

$$l_{11}{}^B = 1.8 \text{ cm}$$

Once these parameters have been calculated, the parameters required make the second system model kinematically behave like the first system model are known. The second system model can then be used to construct a second rotational system (e.g., as a leg prosthesis).

Figure 13:
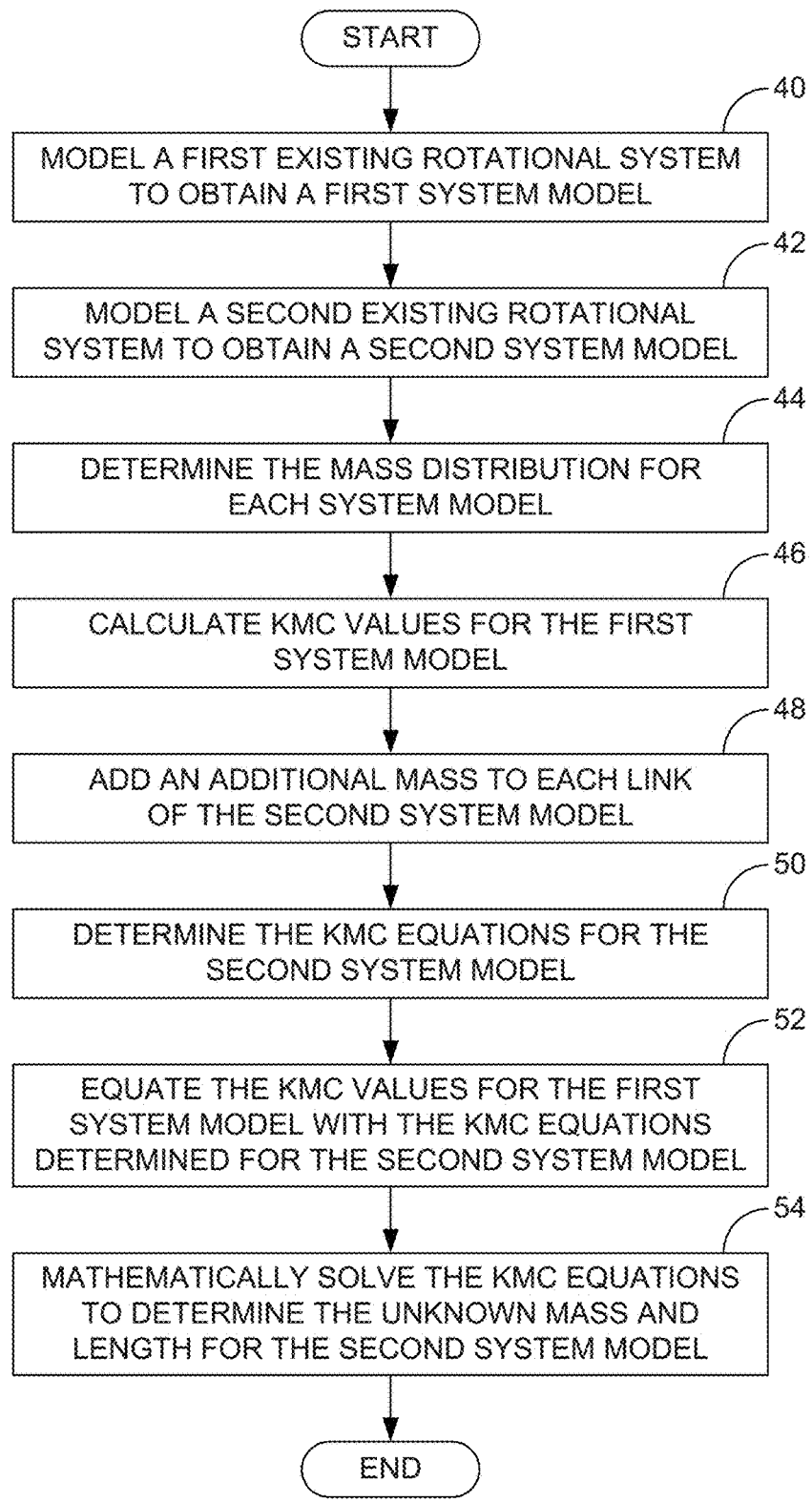
FIG. 13 is a flow diagram of a method for kinematically synchronizing two existing rotational systems.

FIG. 13 is a further flow diagram describing a method for matching the kinematics of two rotational systems. More particularly, FIG. 13 describes a method for synchronizing the kinematics of two existing rotational systems. An example application of this method is determining how to balance the gait of an individual having a growth disorder that has resulted in one leg being heavier than the other leg and this causing an uneven gait. By synchronizing the kinematics of the two legs ("rotational systems"), one can determine how to balance the individual's gait by, for example, adding masses in discrete locations on the individual's lighter leg.

Beginning with block 40 of FIG. 13, a first existing rotational system (System A) is modeled to obtain a first system model (Model A). As before, the system can be modeled as a pendulum. By way of example, the first rotational system can be a heavier leg of a patient having an uneven gait. Referring next to block 42, a second existing rotational system (System B) can be modeled to obtain a second system model (Model B). In keeping with the above-described example, the second rotational system can be the lighter leg of the patient. As in the previous method, the second system model must have the same number of degrees of freedom as the first system model. In addition, in each model, the number of masses on each link must be the same.

With reference next to block 44, the mass distribution for each system model can be determined. This step involves identifying point masses and their locations on their respective links. As before, the parameters of an existing rotational system, and therefore Systems A and B, can be determined by measuring the system. For example, if the existing rotational systems are a patient's legs, each leg can be modeled as a single link having a single mass and the mass distribution can be determined by measuring the moment of inertia of the leg, selecting mass or length values, and calculating the missing mass or length values.

At this point, the KMC values for the first system model can be calculated, as indicated in block 46. As before, these values can be calculated using Equations 4, 7, and 8. In particular, one can input the physical parameters of the mass distributions determined in block 44 for the first system model to obtain the various KMC values. In keeping with the above example, in which the heavier leg has been modeled as a single link having a single mass, the first system model has one degree of freedom and, as indicated in Table 2, there are two KMCs: M and G. As an example, the computed values could be:

$$M_{1,1}{}^A = 30{,}000 \text{ g-cm}^2$$

$$G_1{}^A = 1{,}000 \text{ g-cm}$$

Referring next to block 48, an additional mass can be added to each link of the second system model so that the second system model will have one more mass on each link than the first system model. In keeping with the above-described example, this mass or these masses (depending upon the number of links) are those that can be added to the lighter leg to balance the gait of the patient. The magnitude of the masses and their positions on the leg will be determined through this kinematic matching process.

With reference next to block 50, the KMC equations for the second system model can be determined. This can be accomplished by inputting the known parameters of the second system model into equations 4, 7, and 8. Referring next to block 52, the KMC values for the first system model can be equated to the KMC equations determined for the second system model in block 50. As an example:

$$M_{1,1} = 30{,}000 \text{ g-cm}^2 = (35 \text{ g})(15 \text{ cm})^2 + m_{12}{}^B (l_{12}{}^B)^2$$

$$G_1 = 1{,}000 \text{ g-cm} = (35 \text{ g})(15 \text{ cm}) + m_{12}{}^B l_{12}{}^B$$

At this point, the KMC equations can be mathematically solved to obtain the unknown mass(es) and length(s) of the second system model, as indicated in block 54. As before, this can be accomplished, for example, by solving the equations as a system of linear equations or by using an optimization method. In keeping with the above example, the missing parameters are:

$$m_{12}{}^B = 21 \text{ g}$$

$$l_{12}{}^B = 35 \text{ cm}$$

Once these parameters have been calculated, the second system model is complete and the parameters required make the second system model kinematically behave like the first system model are known. In keeping with the above-described example, the second system model can then be used to determine what masses to add to the lighter leg and where to balance the patient's gait.

In this disclosure, it has been shown that, given the same degrees of freedom and torque input, two dissimilar rotational systems can be motion matched. A minimum of two masses per degree of freedom are required to mimic the motion of a matching system. In essence, this kinematic matching technique can be used to simplify a complicated rotational system. For example, a rotating fan blade, gear, or cam of arbitrary shape can be modeled as one link with two masses, while an open ended chain with any number of links can be modeled as two masses per link. This can greatly simplify computation resulting in the same kinematics.

In humans, animals, and some insects, the limbs can be modeled as swinging pendulums that swing in accordance to their masses and mass distribution. It is possible to manipulate limb movements by simply changing mass and mass distributions such as adding mass to a specific location of the limb. For example, a gait asymmetry (walking limp) can be created in an individual by attaching an extra weight to one leg, while in contrast a symmetric gait can be restored from an asymmetric walking pattern by adding weight to a specific location. With the presented kinematic matching technique, one can match two swinging limbs, such as human legs, so they move symmetrically, but out 180° out of phase. While walking kinematics are the most obvious application, other parts of the body can be synchronized such as swinging arms during walking or moving fingers while playing an instrument or typing on a keyboard. This technique can also be used for the kinematic behavior prediction of swinging robotic limbs.

Wearing a prosthesis that does not have the exact size and weight of the missing limb can create gait asymmetries. Prosthetics research commonly tries to mimic the lost limb in regards to size, weight, and length; however this design constraint can often times seem unrealistic and overconstraining. This design constraint can be alleviated by changing left and right limb mass and mass distribution parameters to obtain symmetric gait with asymmetric limb parameters. As previously stated, the presented kinematic matching technique can analytically match two limbs with symmetric limb mass and mass distribution parameters. That is, one can apply this technique to match the healthy limb with the other limb with a prosthetic by adding masses to one or both limbs, yielding a symmetric gait.

Figure 14:
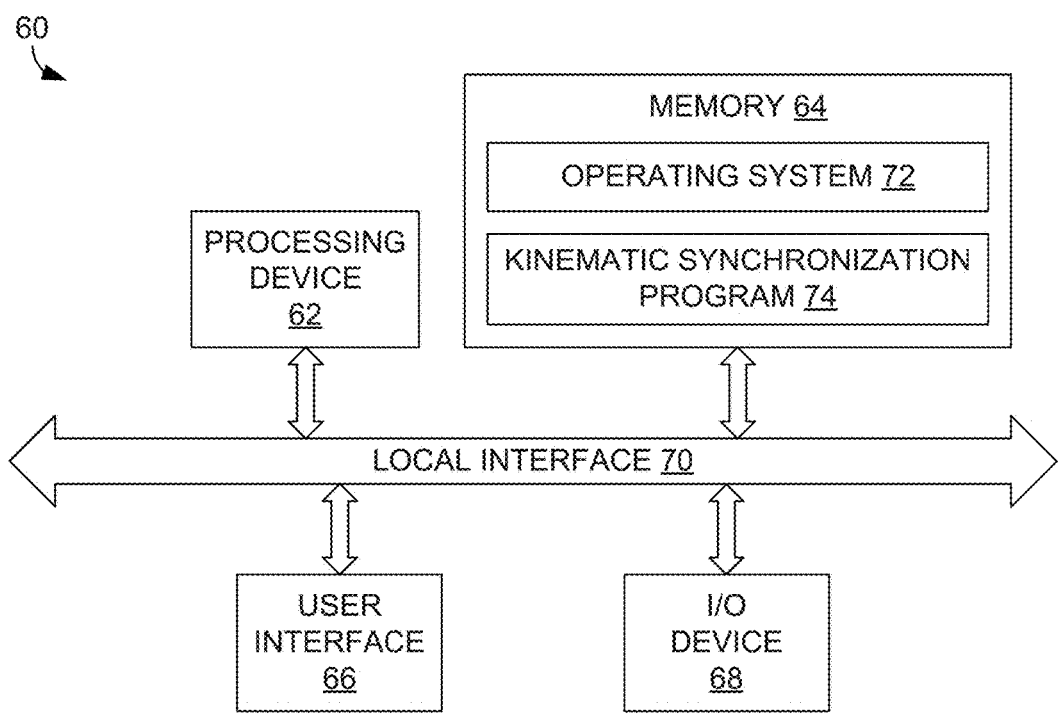
FIG. 14 is a block diagram of a computing system that executes a program that can be used to perform kinematic synchronization of uncoupled, dissimilar rotational systems.

FIG. 14 is a block diagram of an embodiment of a computer system 60 that can be used to synchronize the kinematics of two rotational systems. As shown in this figure, the system 60 generally comprises a processing device 62, memory 64, a user interface 66, and an input/output (I/O) device 68, each of which is connected to a system bus 70.

The processing device 62 can, for example, include a central processing unit (CPU) that is capable of executing instructions stored within the memory 64. The memory 64 includes any one of or a combination of volatile memory elements (e.g., RAM) and nonvolatile memory elements (e.g., hard disk, ROM, etc.).

The user interface 66 comprises one or more devices with which a user interfaces with the computer system 60. The user interface 66 can, for example, comprise a keyboard, mouse, and display. The I/O device 68 comprises a component that enables the system 60 to communicate with other devices.

The memory 64 (a non-transitory computer-readable medium) stores programs (i.e., logic) including an operating system 72 and a kinematic synchronization program 74. The operating system 72 controls the general operation of the computer system 60, while the kinematic synchronization program 74 facilitates the kinematic matching of rotational systems.

The invention claimed is:

1. A method for designing and constructing a limb prosthesis for an individual having an intact limb and an opposite partial limb, the method comprising:
    modeling the intact limb as a first rotational system using an equation of motion to obtain a first system model that represents the intact limb;
    modeling an opposite limb that comprises the partial limb and a limb prosthesis as a second rotational system that is physically dissimilar to the first rotational system using the equation of motion to obtain a second system model that represents the opposite limb;
    matching kinematic matching coefficients of the equations of motion for the first and second system models so they have the same motions to obtain mass and length parameters for the limb prosthesis; and
    constructing a physical limb prosthesis for the partial limb that has the obtained mass and length parameters, wherein, when the limb prosthesis is worn by the individual, the opposite limb has kinematics that match the kinematics of the intact limb.

2. The method of claim 1, wherein the equation of motion is defined as:

$$[M]\ddot{\Theta} + [N]\dot{\Theta}^2 + [G] = [T]$$

wherein [M], [N], [G], and [T] are inertial, damped, gravitational, and forced coefficient matrices, respectively, that contain the kinematic matching coefficients and $\ddot{\Theta}$ is an angular acceleration vector and $\dot{\Theta}^2$ is an angular velocity vector.

3. The method of claim 2, wherein [M] is an inertia matrix defined as $$[M]_{sym}^{\tilde{n},\tilde{n}} = \begin{bmatrix} M_{1,1} & M_{1,2}\cos(\theta_1 - \theta_2) & \cdots & M_{1,j}\cos(\theta_1 - \theta_j) \\ M_{1,2}\cos(\theta_1 - \theta_2) & M_{2,2} & & \vdots \\ \vdots & & \ddots & M_{i-1,j}\cos(\theta_{i-1} - \theta_j) \\ M_{1,j}\cos(\theta_1 - \theta_j) & \cdots & & M_{i,i} \end{bmatrix}$$

wherein $M_{i,i}$ are kinematic matching coefficients.

4. The method of claim 3, wherein [N] is a velocity matrix defined as $$[N]^{\tilde{n},\tilde{n}} = \begin{bmatrix} 0 & M_{1,2}\sin(\theta_1 - \theta_2) & \cdots & M_{1,j}\sin(\theta_1 - \theta_j) \\ -M_{1,2}\sin(\theta_1 - \theta_2) & 0 & & \vdots \\ \vdots & & \ddots & M_{i-1,j}\sin(\theta_{i-1} - \theta_j) \\ -M_{1,j}\sin(\theta_1 - \theta_j) & \cdots & & 0 \end{bmatrix}$$

wherein $M_{1,2}$ are kinematic matching coefficients.

5. The method of claim 3, wherein [G] is a gravity matrix defined as $$[G]^{\tilde{n}} = \begin{bmatrix} \sum_{p=1}^{m} l_{1,p} m_{1,p} \sin(\alpha_{1,p} + \theta_1) + \left(l_1 \sum_{q=2}^{\tilde{n}} \sum_{p=1}^{\tilde{m}} m_{q,p}\right) \sin(\theta_1) \\ \sum_{p=1}^{m} l_{i,p} m_{i,p} \sin(\alpha_{i,p} + \theta_i) + \left(l_1 \sum_{q=i+1}^{\tilde{n}} \sum_{p=1}^{\tilde{m}} m_{q,p}\right) \sin(\theta_i) \\ \sum_{p=1}^{m} l_{\tilde{n},p} m_{\tilde{n},p} \sin(\theta_{\tilde{n},p} + \theta_{\tilde{n}}) \end{bmatrix} g$$

wherein m represents masses, l represents lengths, and α and θ represent angles.

6. The method of claim 1, wherein matching the kinematic matching coefficients comprises equating the kinematic matching coefficients of the equation of motion for the first system model with the kinematic matching coefficients of the equation of motion for the second system model.

7. The method of claim 1, wherein modeling the first and second rotational systems comprises modeling the systems as pendulums.

8. The method of claim 1, further comprising determining a mass distribution for the first system model and calculating the kinematic matching coefficients for the first system model using the mass distribution.

9. The method of claim 8, further comprising determining a mass distribution for the second system model and determining symbolic matching coefficients for the second system model.

10. The method of claim 9, wherein matching kinematic matching coefficients comprises equating the kinematic matching coefficients of the first system model with symbolic kinematic matching coefficients of the second system model to obtain kinematic matching coefficient equations.

11. The method of claim 10, further comprising inserting approximations for one or more masses and mass locations for the second system model in the kinematic matching coefficient equations and mathematically solving the kinematic matching coefficient equations to determine values of unknown masses or mass locations for the second system model.

12. A method for balancing limbs of an individual having a first relatively heavy limb and a second relatively light limb, the method comprising:

modeling the relatively heavy limb as a first rotational system using an equation of motion to obtain a first system model that represents the relatively heavy limb;

modeling the relatively light limb as a second rotational system that is physically dissimilar to the first rotational system using the equation of motion to obtain a second system model that represents the relatively light limb;

matching kinematic matching coefficients of the equations of motion for the first and second system models so they have the same motions to determine magnitudes and positions of masses that are to be added to the relatively light limb to balance the relatively light limb with the relatively heavy limb; and physically attaching masses to the relatively light limb having the determined magnitudes and positions such that, when the masses are attached to the relatively light limb, the relatively light limb has kinematics that match the kinematics of the relatively heavy limb.

13. The method of claim 12, wherein the equation of motion is defined as:

$$[M]\ddot{\Theta}+[N]\dot{\Theta}^2+[G]=[T]$$

wherein [M], [N], [G], and [T] are inertial, damped, gravitational, and forced coefficient matrices, respectively, that contain the kinematic matching coefficients and $\ddot{\Theta}$ is an angular acceleration vector and $\dot{\Theta}^2$ is an angular velocity vector.

14. The method of claim 13, wherein [M] is an inertia matrix defined as $$[M]_{sym}^{\tilde{n},\tilde{n}} = \begin{bmatrix} M_{1,1} & M_{1,2}\cos(\theta_1 - \theta_2) & \cdots & M_{1,j}\cos(\theta_1 - \theta_j) \\ M_{1,2}\cos(\theta_1 - \theta_2) & M_{2,2} & & \vdots \\ \vdots & & \ddots & M_{i-1,j}\cos(\theta_{i-1} - \theta_j) \\ M_{1,j}\cos(\theta_1 - \theta_j) & \cdots & & M_{i,i} \end{bmatrix}$$

wherein $M_{i,i}$ are kinematic matching coefficients.

15. The method of claim 14, wherein [N] is a velocity matrix defined as $$[N]^{\tilde{n},\tilde{n}} = \begin{bmatrix} 0 & M_{1,2}\sin(\theta_1 - \theta_2) & \cdots & M_{1,j}\sin(\theta_1 - \theta_j) \\ -M_{1,2}\sin(\theta_1 - \theta_2) & 0 & & \vdots \\ \vdots & & \ddots & M_{i-1,j}\sin(\theta_{i-1} - \theta_j) \\ -M_{1,j}\sin(\theta_1 - \theta_j) & \cdots & & 0 \end{bmatrix}$$

wherein $M_{1,2}$ are kinematic matching coefficients.

16. The method of claim 14, wherein [G] is a gravity matrix defined as $$[G]^{\tilde{n}} = \begin{bmatrix} \sum_{p=1}^{\tilde{m}} l_{1,p} m_{1,p} \sin(\alpha_{1,p} + \theta_1) + \left(l_1 \sum_{q=2}^{\tilde{n}} \sum_{p=1}^{\tilde{m}} m_{q,p}\right) \sin(\theta_1) \\ \sum_{p=1}^{\tilde{m}} l_{i,p} m_{i,p} \sin(\alpha_{i,p} + \theta_i) + \left(l_1 \sum_{q=i+1}^{\tilde{n}} \sum_{p=1}^{\tilde{m}} m_{q,p}\right) \sin(\theta_i) \\ \sum_{p=1}^{\tilde{m}} l_{\tilde{n},p} m_{\tilde{n},p} \sin(\theta_{\tilde{n},p} + \theta_{\tilde{n}}) \end{bmatrix} g$$

wherein m represents masses, l represents lengths, and α and θ represent angles.

17. The method of claim 12, wherein matching the kinematic matching coefficients comprises equating the kinematic matching coefficients of the equation of motion for the first system model with the kinematic matching coefficients of the equation of motion for the second system model.

18. The method of claim 12, wherein modeling the first and second rotational systems comprises modeling the systems as pendulums.

19. The method of claim 12, further comprising determining a mass distribution for the system models.

20. The method of claim 19, further comprising calculating the kinematic matching coefficients for the first system model using its mass distribution.

21. The method of claim 20, further comprising adding an additional mass to each link of the second system model and determining kinematic matching coefficient equations for the second system model.

22. The method of claim 21, wherein matching kinematic matching coefficients comprises equating the kinematic matching coefficients of the first system model with the kinematic matching coefficient equations for the second system model and mathematically solving the kinematic matching coefficient equations to determine magnitudes and locations for the new masses for the second system model.

* * * * *